Dec. 17, 1974 R. F. MELK Plant Pat. 3,669
GLADIOLUS PLANT
Filed Nov. 17, 1972
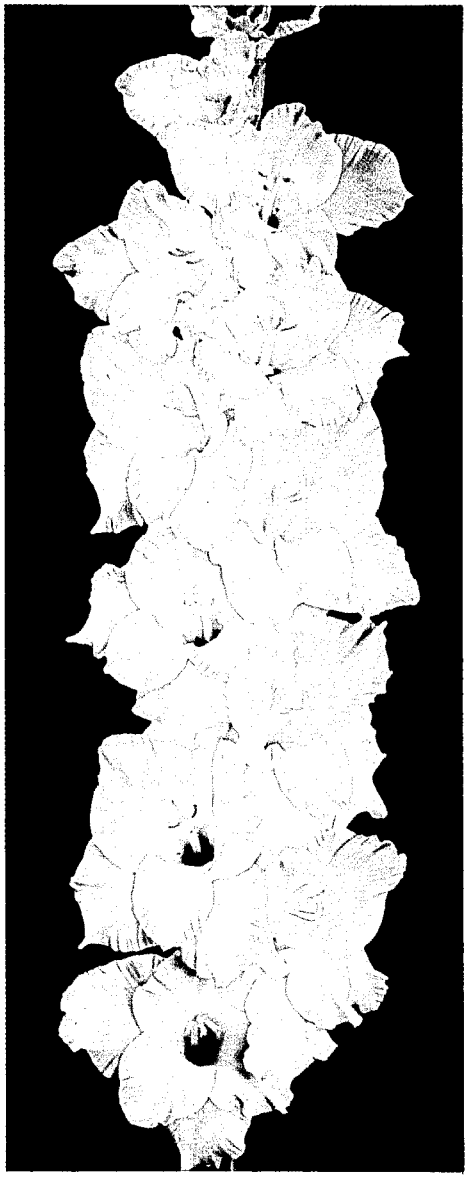

United States Patent Office

Plant Pat. 3,669
Patented Dec. 17, 1974

3,669

GLADIOLUS PLANT

Ruth F. Melk, Mequon, Wis. 53092

Filed Nov. 17, 1972, Ser. No. 307,546
Int. Cl. A01h 5/00
U.S. Cl. Plt.—85 1 Claim This invention relates to a new and distinct variety of gladiolus plant.

This new gladiolus plant was originated by me by crossing a seed parent known as "Pride of Wisconsin" (Pat. No. 2,218) with a pollen parent which was of unknown origin.

The improved variety resulting from this breeding is evidenced by the following unique combination of characteristics which are outstanding therein and which distinguish my new variety from its parents, as well as from other varieties of which I am aware:

First: A color combination so unique and distinctive that no other variety resembles mine.
Second: A variety which is extremely early in blooming.

In addition to these major characteristics my variety is also endowed with the following characteristics:

1. Good bud count opening many florets at one time.
2. Along with a stem free from crooking, extremely uniform spikes are formed, from one plant to another.
3. Admirable and consistent growth habits.
4. Excellent propagative powers.
5. Strong plant relative to weather and wind.

I have asexually reproduced the new variety by cormels through several generations in Wisconsin, and succeeding generations have established that the distinguishing characteristics of the variety held true. By natural increase from cormels through several generations its color and other characteristics have proven to be permanently fixed.

The accompanying drawing shows a typical specimen of a flower spike of the new variety, with the flowers in varied stages of growth. Some are shown as partially opened buds and others as fully opened buds. The colors depicted are as nearly true as is possible to achieve in this type of reproduction.

The following is a detailed description of my new variety, with color terminology in accordance with the Horticultural Colour Charts issued by the British Colour Council and the Royal Horticultural Society, except where general color terms of ordinary dictionary significance are obvious.

PLANT

Growth: Healthy, vigorous and consistent: good propagator, attaining a height of 60 inches.

Blooming Habit: The flower blooms extremely early. Under normal conditions in the midwest the first bloom appears approximately 65 days rather than the usual 80 to 85 days after planting, with about 10 florets showing color at one time.

Stems:
- *Form.*—Fairly tall and straight.
- *Diameter at base.*—About ½ inch.
- *Color at base.*—Green.

Foliage: Above the ground the plant has short green leaves. The average leaf is one and one-half inches wide at the base, and the foilage excluding the flower spike grows about 16 inches long, the leaves tapering gracefully to a point.

Disease Resistance: The variety has been found to be unusually resistant to the usual gladiolus plant diseases of a bacterial, viral or fungoid genesis.

Corms: Mature corms are round with smooth firmly attached husks which have a rose cast.
- *Color of flesh.*—Yellow with a pencil line of rose where the husk is attached to the bulb.

FLOWER

Spike:
- *Form and size.*—Tall and straight with a flowerhead length of 24 inches, regularly carrying 20 to 22 buds.

Bud:
- *Size.*—About 2½ inches long when opening.
- *Opening.*—On first blooming 3 or 4 buds open with 2 or 3 a day opening thereafter.

Flower:
- *Arrangement.* — Flowerhead of the new variety has a formal placement.
- *Size.*—Individual florets average about 4½ inches in diameter.
- *Form.*—Florets are slightly round, and gently ruffled.
- *Keeping qualities.*—The flowers keep better than average, and open exceptionally well from tight buds.

Petals:
- *Shape.*—Somewhat round, but slightly recurved.
- *Size.*—Upper petals—about 2 to 2½ inches wide. Lip petals—about 1½ to 2 inches wide.
- *Aspect.*—Substance is average. Surface is uneven and slightly ruffled.
- *Fragrance.*—None.
- *Color.*—The petals of this variety are unusual in color being predominantly rose colored — Tyrian rose — plate 454, with a silver border — plate 400 — around the outside of each petal, some petals also having silver throat blotches.

REPRODUCTIVE ORGANS

Stamens:
- *Color.*—White and black.

Pistils:
- *Color.*—White.

GROWTH

Locality where grown and observed: Mequon, Wis.

Propagation: Holds its distinguishing characteristics through succeeding propagations from cormels.

It can be seen that this variety is unique in its rose color with a silver border, and in the fact that it blooms extremely early, in sixty-five to seventy days.

What I claim is:

1. A new and distinct variety of gladiolus plant, substantially as herein shown and described, characterized particularly as to novelty by the unique combination of its unique color, which is predominantly rose but with a silver border, and its early blooming habit.

No references cited.

ROBERT E. BAGWILL, Primary Examiner